Figure 1:
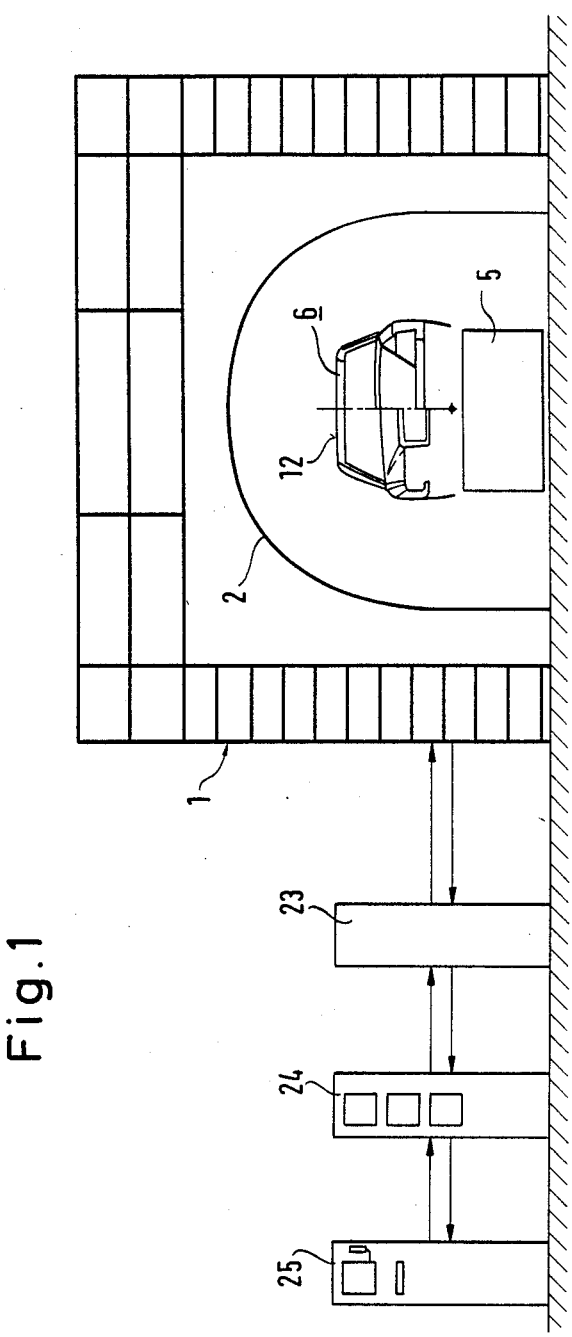

United States Patent

Klenk et al.

[11] Patent Number: 4,918,321
[45] Date of Patent: Apr. 17, 1990

[54] REFLECTED LIGHT SCANNING METHOD AND APPARATUS FOR THE DETECTION OF SURFACE BLEMISHES

[75] Inventors: Jürgen Klenk, Alling; Horst Krasowski, Stuttgart; Gerhard Jünemann, Leonberg, all of Fed. Rep. of Germany

[73] Assignees: Roth-Electric GmbH; Daimler-Benz AG, both of Fed. Rep. of Germany

[21] Appl. No.: 180,936

[22] Filed: Apr. 13, 1988

[30] Foreign Application Priority Data

Apr. 13, 1987 [DE] Fed. Rep. of Germany ....... 3712513

[51] Int. Cl.⁴ ........................................... G01N 21/86
[52] U.S. Cl. ..................................... 250/571; 356/445
[58] Field of Search ............... 250/562, 563, 571, 572; 356/430, 431, 376, 445, 448

[56] References Cited

U.S. PATENT DOCUMENTS 3,800,148  3/1974  DeCock ............................. 250/562
4,260,899  4/1981  Baker ................................ 250/563
4,528,455  7/1985  Loose ................................ 250/563
4,549,206  10/1985  Suzuki et al. ..................... 250/563
4,563,095  1/1986  Puffer ............................... 250/562

Primary Examiner—David C. Nelms
Attorney, Agent, or Firm—Sughrue, Mion, Zinn, Macpeak & Seas

[57] ABSTRACT

In a method for the detection of blemishes on the surface of an object, e.g. for the detection of blemishes in the paintwork on the surface of a motor vehicle body, a strip of light is produced on the surface by means of a lighting system, and this strip of light is moved over the surface by relative movement between the lighting system and the surface; strip-like sections of the surface of the object are in each case recorded stepwise in the region of the strip of light, the step size of successive recordings being smaller than the width of the strip of light. In an apparatus for carrying out this method, the lighting system comprises at least one lighting unit with a light exit window, and the recording system comprises at least one sensor unit with a light entry window, the light exit window and the light entry window being arranged closely adjacent.

15 Claims, 4 Drawing Sheets

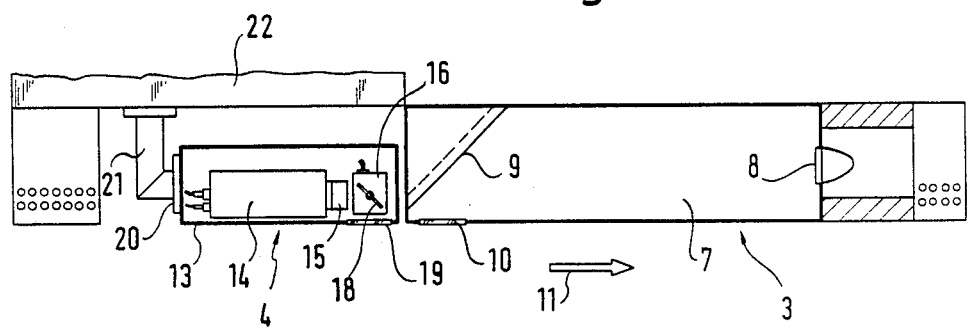
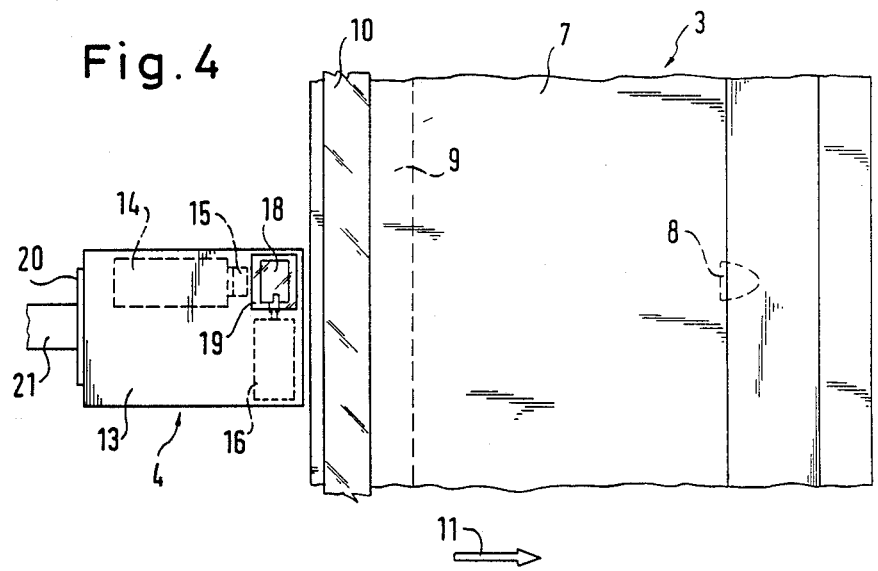

REFLECTED LIGHT SCANNING METHOD AND APPARATUS FOR THE DETECTION OF SURFACE BLEMISHES

The invention relates to a method for the detection of blemishes on the surface of an object, e.g. for the detection of blemishes in the paintwork on the surface of a motor vehicle body or on the surface of other industrially produced objects, in which a strip of light is produced on this surface by means of a lighting system, and this strip of light is moved over the surface by relative movement between the lighting system and the surface. Furthermore, the invention relates to an apparatus for carrying out this method.

Methods and apparatuses of this kind are known, for example, from West German Patent 34 18 317. They are connected with the drawback that certain surface blemishes, particularly smaller ones, can be detected only with difficulty due to low contrasts during analysis of the reflected light affected by surface blemishes. For example, this is the case when the gloss of the surface to be examined is not optimal.

According to the aforementioned West German Patent 34 18 317, it has already been proposed to provide several rows of lights adjacent to each other for carrying out the method mentioned hereinbefore. By producing several strips of light at intervals from each other on the surface to be examined, during relative movement between this surface and the lighting system a surface blemish should pass successively through several strips of light and be easier to detect visually by repeated appearance in the successive strips of light. However, this method demands maximum attention from the examining personnel continuously and is therefore very tiring in the long run, without providing sufficient guarantee of largely complete detection of blemishes which are more difficult to detect as well.

According to U.S. Pat. No. 46 29 319, it has also already been proposed, in the surface illumination of surfaces for the detection of blemishes, to obtain an increase of contrast in the reflected test light by using so-called reflector films which are introduced into the path of the beam of reflected light and reflect the light impinging on such a film with a certain scatter characteristic, whereupon after repeated reflection at the surface to be examined it passes to a video camera. This method, however, requires a large angle of incidence for the test light, which considerably increases the space requirements for the whole testing assembly, so that practical use in confined space conditions on the test stand poses problems. Moreover when examining curved surfaces, changes in the topography as a result of the large angle of incidence of the test light rapidly lead to considerable distortions which counteract reliable detection of blemishes.

It is the object of the invention to provide a method and an apparatus of the kind mentioned hereinbefore which allows reliable detection of blemishes on or in surfaces of motor vehicles and other objects, even when the surface, as in the case of undercoating for motor vehicle bodies, is matt and therefore causes greater scattering of the reflected light. Nevertheless the testing assembly is to be space-saving and therefore versatile and move the production costs predominantly into the electronic range in which a clearly decreasing trend in costs is generally to be expected. Furthermore, easy handling of the testing assembly is to be achieved, which to a large extent relieves the stress on testing personnel.

According to one aspect of the invention, there is provided a method for the detection of blemishes on the surface of an object, e.g. for the detection of blemishes in the paintwork on the surface of a motor vehicle body, in which a strip of light is produced on the surface by means of a lighting system, and this strip of light is moved over the surface by relative movement between the lighting system and the surface, characterised in that strip-like sections of the surface of the object are recorded stepwise, each time in the region of the strip of light, the step size of successive recordings being smaller than the width of the strip of light.

According to another aspect of the invention, there is provided apparatus for carrying out the method characterised in that the lighting system comprises at least one lighting unit with a light exit window and the recording system comprises at least one sensor unit with a light entry window, and light exit window and light entry window are arranged closely adjacent.

Figure 2:
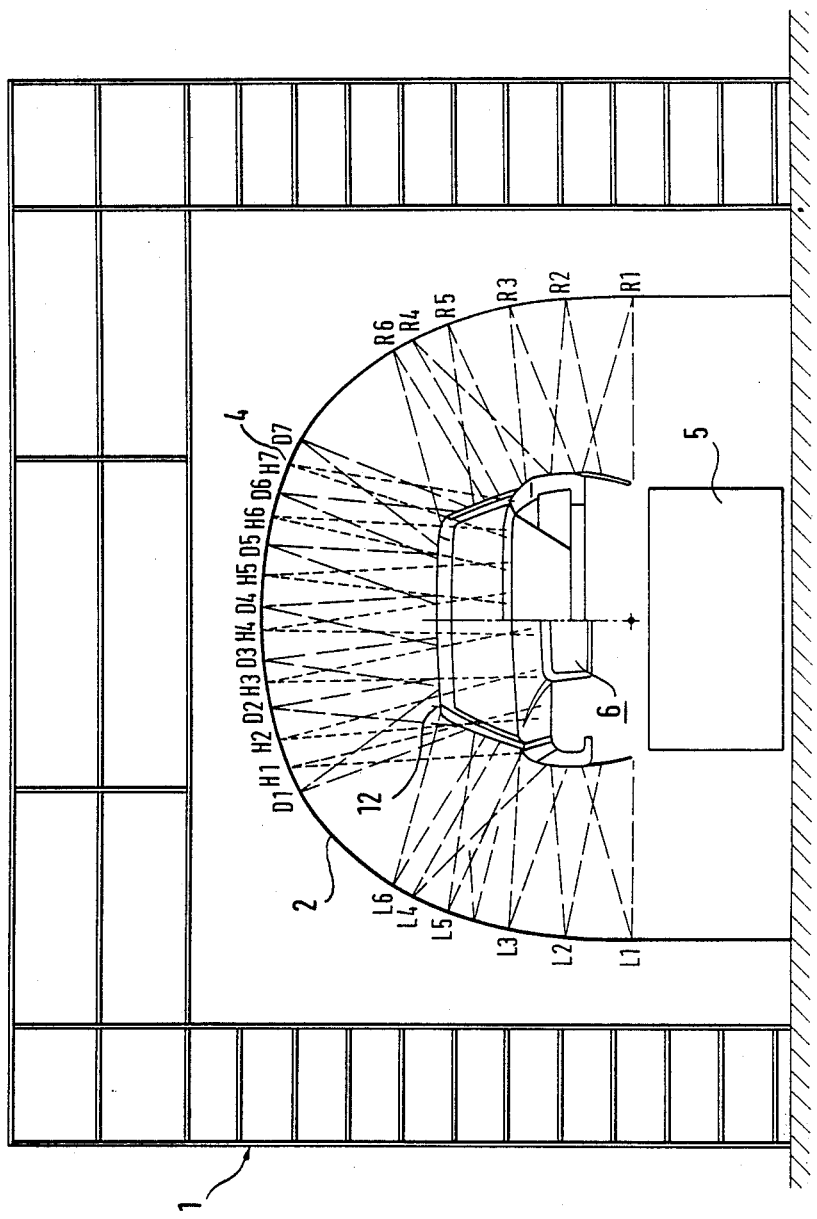
Figure 5:
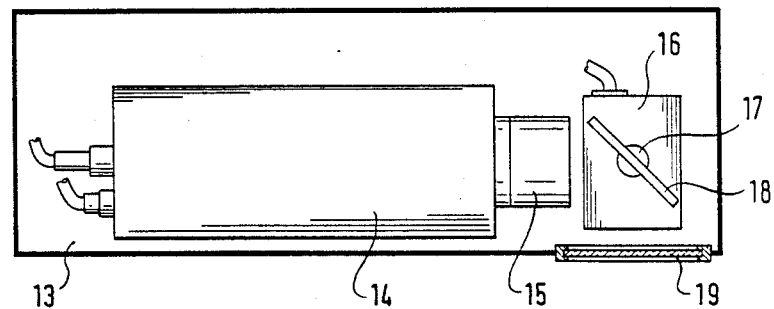
Figure 6:
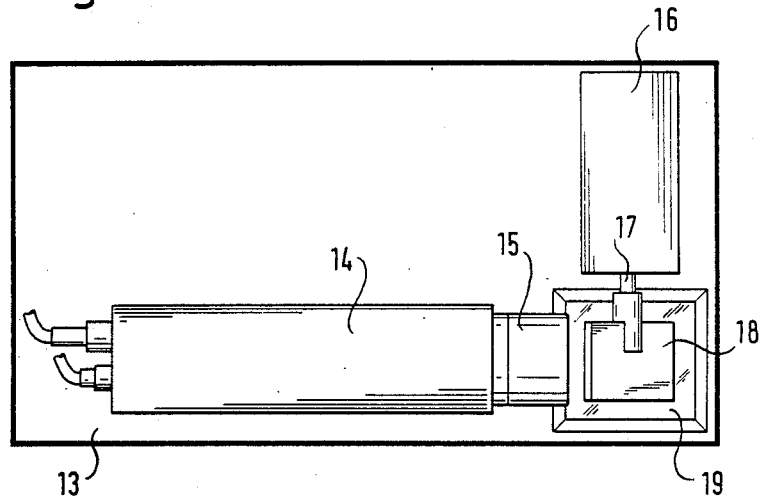
Figure 7:
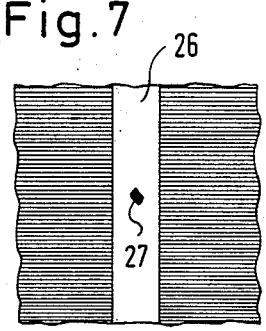

A preferred embodiment of the method and apparatus according to the invention for the detection of blemishes in the paintwork on the bodies of motor vehicles is described in more detail below with reference to the attached drawings, in which:

FIG. 1 shows a test stand for the detection of surface blemishes in elevation, with computers shown schematically, FIG. 2 shows the test stand of FIG. 1 in an enlarged view with sensor units shown schematically, FIG. 3 shows a lighting unit and a sensor unit from FIG. 2 shown in detail, FIG. 4 shows the lighting and sensor units of FIG. 3 in a view from below, FIG. 5 shows the sensor unit from FIG. 3 in an enlarged view, FIG. 6 shows the sensor unit of FIG. 5 in a view from above, and FIG. 7 shows the reproduction of an image of the scan of the surface examined, which appears on a monitor of the sensor unit.

In FIGS. 1 and 2 is shown a test stand with a frame 1 which, for example, is formed by tubes or profile members bolted together. In the interior of the frame 1 is drawn a portal 2 as an arcuate line. Along this arcuate line are disposed several lighting units 3 and sensor unit 4 respectively. These units are attached to the frame 1 by brackets, not shown, in such a way that their arrangement along the arcuate line of the portal 2 is guaranteed. The lighting units 3 together form a lighting system, while the sensor units 4 together form a recording system, as will be described in more detail below.

The dimensions of the portal 2 are such that the body 6 of a passenger car can be passed on a carriage 5 through the portal perpendicularly to the plane of drawing of FIGS. 1 and 2 and is spanned by this portal, the body maintaining its side and roof sections an approximately uniform distance from the respectively opposed portal sectors. In FIGS. 1 and 2, the body 6 of the car is shown in its left half with the front, and in its right half with the rear. It is placed on the carriage 5 without wheels by mounting means, not shown. The carriage 5 can be moved with the car body 5 mounted on it slowly and as evenly as possible through the portal 2 on rails (not shown) extending perpendicularly to the plane of drawing, for which purpose it is provided with a chain drive, also not shown.

Along the arcuate line of the portal 2 are located about 30 lighting units 3 of identical design. One of these lighting units is shown in more detail in FIGS. 3 and 4.

The lighting unit 3 comprises, in a shaft-like housing 7 whose surfaces are painted matt black, a halogen lamp 8 which is cold-metallised and produces a light cone of about +/−20°. The light emerging from the lamp 8 impinges on a special reflector 9 which is inclined at an angle of about 45° to the optical axis of the lamp 8 and guides the light towards an exit window 10 which is disposed in the shaft-like housing 7 and through which the light is guided onto the surface of the car body 6. The reflector 9 acts as a mirror for light beam components parallel to the drawing plane of FIG. 3, and has a diffuser for light beam components perpendicular to the drawing plane.

The direction in which the car body 6 is moved through the portal 2 is marked by the arrow 11 in FIGS. 3 and 4. The light exit window 10 is relatively narrow parallel to the arrow 11, but relatively large perpendicularly thereto.

The lighting units 3 are disposed on the portal 2 in such a way that the light exit windows 10 of adjacent lighting units 3 abut against each other by their edges, so that along the line of the portal 2 is formed a continuous narrow light band which approximately follows the line of the portal in a polygonal course. If the car body 6 is guided on the carriage 5 through the portal 2, the cross-sectional profile of the car body which is located at any given time beneath the portal 2 in uniformly illuminated in the form of a narrow continuous light band which extends on the narrow section of the surface 12 of the body 6 belonging to the upper cross-sectional profile, perpendicularly to the direction of transport, from the lower edge of one side over the roof or bonnet portion of the lower edge of the other side of the body. The light band produced on the body surface 12 has a width of about 50–100 mm. On travelling through the portal, the car body 6 passes under this light band and is illuminated by it in strips.

Furthermore, on the portal 2 closely adjacent to the lighting units 3 are located 26 sensor units 4 which are used for optical scanning and recording of images in strips of the surface sections of the car body 6 which are illuminated by the lighting units 3. The sensor units 4 are distributed over the arc of the portal in such a way that with their recording angle together by completely cover all portions of the cross-sectional profile of the car body 6. Here, the sensor units L1 to L6 and R1 to R6 are used to cover the left and right side surfaces of the car body 6 respectively, while the sensor units D1 to D7 and H1 to H7 are used to cover the upwardly facing roof and bonnet surfaces. The sensor units 4 are designed essentially the same as each other. They differ only with respect to focussing of the cameras which they contain and which are described in more detail below, on different distances of the car body regions covered by them, to allow for the fact that the regions of the bonnet and boot lid of the body are further away from the portal arch than the roof and side regions.

One of the sensor units 4 is also shown in more detail in FIGS. 3 and 4. It includes an assembly plate 13 on which are disposed a video camera 14 equipped with a matrix CCD, with a picture-taking lens 15, and a sensor 16 with a scanning mirror 18 which is rotatable about an axis 17. The CCD components of the video camera 14, which are arranged in a matrix, form optoelectronic transducers for video conversion of the incoming analogue light signals to digital electrical signals. Moreover, the assembly plate 13 carries an anti-reflection light entry window 19 behind which the disposed the scanning mirror 18 of the scanner 16. The scanning mirror 18 deflects the light emerging from the lamp 8 and reflected by the surface 12 of the car body 6, after passage through the light entry window 19, into the lens 15 of the camera 14.

The scanning mirror 18 of the scanner 16 is driven with computer control by a drive system not shown in more detail, and has an angular velocity of about 0.5 revolutions per minute. It compensates the movement blur which would arise during photographing of the body surface 12 during transport by the carriage 5 without such compensation. Furthermore, irregularities in the rate of advance of the carriage 5 when driving is jerky can be compensated by corresponding additional means for regulating movement of the scanning mirror 18, if such speed variations are registered e.g. by a tachogenerator, which is known in the art and not shown, at the pinion of a chain which drives the carriage 5, and corresponding signals are fed to the scanner control system of all sensor units 4.

If, in curved surface regions of the car body 6, the angle of incidence for the scanning light coming from the lighting units 3 varies during transport of the car body through the portal 2, the image of the light band produced on the car body, which is adjusted to the image centre of a monitor connected to the video camera 14, drifts away from the image centre. In order to prevent this, the scanner 16 of the sensor unit 4 also has the task of preventing such drift of the light band image away from the image centre of the monitor, by appropriate control of the scanning mirror 18.

The assembly plate 13 is releasably attached to a carrier plate 20 which is mounted adjustably on an angle bracket 21, using fastening means which are well known and therefore not shown. The angle bracket 21 in turn is located on a fitting 22 by which the sensor unit 4 is attached to the portal 2.

The sensor unit 4 is preset before attachment to the carrier plate 20, and thereafter adjusted finally by adjustment of the carrier plate 20 relative to the angle bracket 21. This final adjustment is independent of the respective model of vehicle to be examined. When final adjustment has been carried out, the carrier plate 20 can be prevented from further movement relative to the angle bracket 21 by adhesion, bolting or pinning. This has the advantage that a defective sensor unit 4 can be removed from the carrier plate 20 and replaced by a new, identical, preset sensor unit, without losing the adjustment of the whole assembly.

Adjustment of the whole assembly of each sensor unit 4 on the portal 2 is carried out in such a way that the recording zones of the video cameras of adjacent sensor units overlap on the surface 12 of the car body 6, as can be seen from FIG. 2. As a result, during checking of the body surface for blemishes in the paintwork, which is described in more detail below, no area of this surface is omitted or left unexamined. Furthermore, during adjustment care must be taken to ensure that the image of the light band produced on the body surface, which image appears on the monitors connected to the video cameras, is approximately at the image centre when covering surface regions oriented perpendicularly to the cross-sectional profile of the body. Drifting of the light band away from the image centre in case of curved surface regions is, as already mentioned, prevented by computer control of the scanner 16.

As can be seen from FIGS. 3 and 4, the lighting units 3 and the sensor units 4 are arranged closely adjacent to each other on the portal 2, so that the light entry windows 19 of the sensor units 4 lie closely adjacent to the light exit windows 10 of the lighting units 3 in the same plane. The light emerging from the lighting units 3 is thus reflected at the body surface 12 at a very low angle of reflection to the sensor units 3. As a result, distortions at the convex and concave surface regions of the body 6 remain small.

Each video camera of each sensor unit 4 is connected to a separate camera computer. These camera computers, which can be taken from the commercially available computer range, are, as can be seen from FIG. 1, housed in a first cabinet 23. However, in the embodiment shown in FIG. 2 with 26 sensor units, the number of camera computers can be reduced from 26 to 19 if the computers of the cameras of sensor units D1 to D7, which are used to scan the roof surfaces of the body 6, are alternately also connected to the cameras of sensor units H1 to H7, which are used to scan the bonnet surfaces of the body 6. This is possible cause the roof and bonnet surfaces of the body 6 in a plan view do not overlap, and therefore the sensor units D1 to D7 and the sensor units H1 to H7 never become operative at the same time, but always alternately. The computers of the cameras control the scanners 16 of the sensor units 4 and analyse the image signals generated by their video cameras.

The output signals of the camera computers mounted in the cabinet 23 are passed to intermediate computes which according to FIG. 1 are housed in a cabinet 24 and which further process data from the sensor groups L1 to L6, R1 to R6 and D1/H1 to D7/H7 until they are transmitted to a main frame computer 25. The monitors installed in the cabinet 24 can be switched alternately to all the sensor units 4, in order to monitor the original image.

In the main frame computer 25, all measurement data are compiled. It is equipped with a data output station which prints out information on detected surface blemishes.

With this arrangement, a testing operation proceeds as follows. The body 6 of a car to be examined for blemishes in the paintwork is placed outside the portal 2 on the carriage 5 which can travel the appropriate distance, preferably with its front towards the portal. Then the lighting units 3 and sensor units 4 as well as the drive for the carriage 5 are switched on, whereupon the body 6 moves on the carriage 5 into the portal 2 and passes through the latter at the rate of advance of the carriage drive. In the embodiment described, the rate of advance of the carriage 5 is about 50-100 mm/sec.

The narrow light band which is produced by the lighting units 3 travels over the surface 12 of the body 6, and illuminates a narrow strip 50-100 mm wide respectively in a cross-sectional profile of the body. The sections of the body surface 12 located beneath the light band on the respective cross-sectional profile are each covered by a video camera 14 of the sensor units 4.

The camera computers mounted in the cabinet 23 automatically cause the video cameras associated with them to record simultaneously, every 10 mm of advance of the body through at any given time. At the rate of advance in the above-mentioned range (50-100 mm/sec), this results in about 5 images per second. If the body 6 has a normal length of 4 m, then accordingly each video camera during travel of a body through the portal 2 stepwise delivers a total of 400 shots, i.e. 400 cross-sectional profiles are scanned stepwise between the front and rear ends of the body 6 and recorded. As these recordings succeed each other in steps of 10 mm each, and the light band produced on the body surface 12 for scanning has a width of 50-100 mm, on account of the step size of the recording sequences, which is substantially smaller than the width of the light band, it is ensured that no section of the body surface 12 remain uncovered. On the contrary, the images of the surface sections succeeding each other in the time overlap in their image content by about 70% in each case.

In order to avoid elaborate exposure control at the lenses of the video cameras 14 of the sensor units 3, the lamps 8 of all lighting units 3 can be controlled or regulated jointly in such a way that the intensity of the light emerging from them and reflected by the surface 12 of the body 6 is adapted to the lighter or darker colour of the body paintwork. As a result, the intensity of the light incident on the video cameras can be maintained roughly constant in all cases.

On the monitors which can be connected to the video cameras 14 of the sensor units 4, blemishes on the surface of the body 6 appear either as dark areas in the light image of the light band produced on the body 6, or as changes in the contour of the image of this light band. FIG. 7 shows a recording of such a monitor image. There, the image of the light band is marked 26, a blemish in the paintwork appearing as a dark area 27.

The data of the partial images of the individual surface sections of the cross-sectional profile covered at any given time, which are recorded simultaneously by the video camera 14 of the sensor units 4, and the data of the thus detected images of the cross-sectional profiles of the body 6 passing successively beneath the light band, are further processed in the computers and compiled into an overall image which is output by the data output station of computer 25, for example, as a hard copy printout, and which gives information on any blemishes on the whole surface of the body 6 and on the coordinates of these blemishes.

With the aid of this information, the blemishes detected with the above system on the surface of the body being examined can then easily be found and eliminated by the personnel in charge of eliminating blemishes, if visual detection of these blemishes is difficult by itself.

In order that surface blemishes which occur on the surface 12 of the body 6 in the overlap zone of the video cameras 14 of two adjacent sensor units 4 are not signalled twice by the system described, the following method can be employed.

Before putting the proposed arrangement into operation for detection of surface blemishes of the bodies of a particular vehicle model to be examined in series, first a light-coloured body sample of this vehicle model is placed in the portal 2 successively, preferably at four points (front region, door region, rear region), and in each case illuminated with the light band produced by the lighting units 3. In the first of these four positions, the two monitor images of adjacent sensor units 4 are each observed, so that roughly in the middle of the overlap zone a marking, e.g. with black felt-tip pen, can be applied to the sample body, which can be traced and monitored on the monitor images. In this way the overlap zones of all sensor units L1/2 to R2/R1 of the portal are marked on the sample body. The same marking operations are repeated in the following second to fourth positions of the sample body. Thus there are obtained, e.g. on each side panel of the sample body, 20 marking points which are arranged in 5 lines. Then the four marking points in each line are joined, in each case by hand, to form a continuous black line from front to rear, for which no special care need be taken. Thus the whole surface of the sample body is covered, on the two side surfaces and on the roof and bonnet surfaces, with a total of 16 marking lines extending from front to rear. This sample body marked in this way is now moved out of the portal 2 and then again introduced into the portal 2 and passed through the portal 2 in a regular testing operation as described above.

A special starting programme of the computers now detects in each image which is produced by the sensor units 4 a maximum of 2 marking lines, and thus in each case fixes exactly the measurement range of each sensor unit 4 at each point of the body surface of the vehicle model represented by the marked sample body.

The recording range of the video cameras 14 of any two adjacent sensor units 4 is thus limited with this starting program in such a way that the recording range of one camera remains below, and the recording range of the other camera remains above one and the same marking line.

After this starting program, regular examination of the bodies of the respective vehicle model coming off the assembly line in series can be recorded, as described above. Due to restriction of the overlapping recording ranges of the video cameras, which is carried out by means of the sample body, detection of a blemish twice is prevented, without the bodies examined in series with the proposed assembly having to be marked again.

The sample body marked by the method described above thus serves to review the system and is kept for possible subsequent readjustments.

Naturally it is necessary to provide a separate sample body for each vehicle model which differs from other vehicle models in the design of its body, and to adjust the software of it by means of the respective starting programme.

Instead of passing the movably mounted carriage 5 with the body 6 through the stationary portal 2, the body 6 can remain stationary and the portal 2 can be moved over the body 6 after being equipped with a rail mechanism. The only essential thing is that relative movement takes place between the body 6 and the portal 2 with the lighting units 3 and the sensor units 4.

With the proposed apparatus, the front and rear of vehicle bodies can also be examined for surface blemishes, if additional and suitably arranged sensor units are provided for this in front of and behind the portal 2.

Finally, the method and apparatus according to the invention are also suitable, if adapted accordingly, for the detection of blemishes on surfaces of other industrially made objects, for example, objects made of flat or hollow glass, ceramics, plastics, etc. or kitchen appliances and other commodities of which the buyer or user expects perfect surfaces.

LIST OF REFERENCE NUMBERS

1 = frame
2 = portal
3 = lighting unit
4 = sensor unit
5 = carriage
6 = body
7 = housing
8 = lamp
9 = reflector
10 = light exit window
11 = arrow of direction
12 = body surface
13 = assembly plate
14 = video camera
15 = lens
16 = scanner
17 = mirror axis
18 = scanning mirror
19 = light entry window
20 = carrier plate
21 = angle bracket
22 = fitting
23 = housing for camera computers
24 = housing for intermediate computers
25 = main frame computer
26 = light band image
27 = blemish

We claim:
1. A method for monitoring a substantially smooth surface of an object for surface defects comprising:
providing relative movement between said object and lighting means;
illuminating a narrow strip on a surface of said object with diffused light from said lighting means with said strip being disposed transverse to the direction of relative movement;
directing light reflected from said surface into opto-electronic video camera means mounted adjacent said lighting means to produce images of said surface of the object being monitored;
said directing of said reflected light being carried out by means of movable reflecting means to provide a series of images of the surface of the object being monitored, whereby the increment of movement between adjacent images is smaller than the width of said narrow strip of light to provide overlapping of said images; and
evaluating video signals provided by said opto-electronic video camera means for intensity variations indicative of surface defects.

2. A method according to claim 1, wherein said directing of reflected light by said movable reflecting means is carried out by moving said movable reflecting means in synchronism with the relative movement between said object and said lighting means to prevent blurring of said images.

3. A method according to claim 1, further comprising providing a sharp contrast between edges of the illuminated strip along both sides perpendicular to the direction of relative movement and evaluating edges of each image of said strip for disruptions in linearity in the video image by said computer means.

4. A method according to claim 1, further comprising a plurality of lighting means adjacent each other perpendicularly to said direction of relative movement in the form of an arch to provide a continuous illuminated strip on the surface of the object and providing a plurality of monitoring means adjacent said lighting means for simultaneously providing images of the continuous strip.

5. An apparatus for monitoring a substantially smooth light reflecting surface of an object for surface defects comprising lighting means for emitting defused light substantially perpendicular to the surface of the object to be monitored, sensor means mounted adjacent said lighting means for receiving light reflected from said surface, transport means for moving said object to be mounted and said lighting means relative to each other, said lighting means having means for providing a narrow strip of light transverse to the direction of relative movement between said object and said lighting means, said sensor means comprising opto-electronic video camera means fixedly mounted adjacent said lighting means, movable reflecting means for reflecting light reflected from said surface to said camera means and means for moving said reflecting means sequentially in synchronism with said relative movement between said object and said lighting means to provide a consecutive series of still images of the surface wherein the spacing of the consecutively occurring images as measured on the surface of the object to be monitored is smaller than the width of said images in the direction of relative movement whereby said images overlap each other and computer means connected to said camera means to provide on-line evaluation of said images for changes in intensity indicative of surface blemishes.

6. An apparatus according to claim 5, wherein said surface of said object is the surface of a painted automobile body.

7. An apparatus according to claim 5, wherein said lighting means is comprised of a lamp, an angled mirror for reflecting light from said lamp and a defuser disposed perpendicular to the path of the light reflected from said mirror.

8. An apparatus according to claim 5, wherein said light means is comprised of a plurality of lamp, mirror and defuser combinations disposed in close proximity to each other perpendicular to the direction of relative movement to provide a continuous strip of light on the surface of said object.

9. An apparatus according to claim 8, wherein said continuous strip of light at least partially circumscribes said object.

10. An apparatus according to claim 8, wherein said continuous strip of light is at least approximately adapted to a cross-sectional profile of said object.

11. An apparatus according to claim 8, wherein said plurality of lamp, mirror and defuser combinations form an arch which is adapted to span the object being examined.

12. An apparatus according to claim 8, wherein said plurality of lamps are provided with means for jointly controlling the intensity of the light produced by said lamp.

13. An apparatus according to claim 5, wherein said movable reflecting means is comprised of a mirror mounted for pivotal movement disposed between said camera means and said object.

14. An apparatus according to claim 5, wherein said sensor means is comprised of a plurality of units each including said camera means and said movable reflecting means with each unit adapted to monitor an area on the surface of the object, which areas are linked with each other.

15. An apparatus according to claim 14 further comprising calculator means associated with said sensor means for producing an overall image from the individual images recorded within individual camera means.

* * * * *